US 7,022,330 B2

(12) United States Patent
Bandyopadhyay et al.

(10) Patent No.: US 7,022,330 B2
(45) Date of Patent: Apr. 4, 2006

(54) PARENTERAL FORMULATION FOR EPOTHILONE ANALOGS

(75) Inventors: Rebanta Bandyopadhyay, Portage, MI (US); Timothy M. Malloy, Yardley, PA (US); Andrea Panaggio, West Windsor, NJ (US); Krishnaswamy Srinivas Raghavan, Cranbury, NJ (US); Sailesh Amilal Varia, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 147 days.

(21) Appl. No.: 10/051,727

(22) Filed: Jan. 17, 2002

(65) Prior Publication Data

US 2002/0143038 A1    Oct. 3, 2002

Related U.S. Application Data

(60) Provisional application No. 60/264,228, filed on Jan. 25, 2001.

(51) Int. Cl.
*A61K 9/00* (2006.01)

(52) U.S. Cl. ............... 424/400; 424/422; 514/365; 514/37; 514/183; 548/146

(58) Field of Classification Search ............... 424/400, 424/422; 514/183, 37, 365; 548/146
See application file for complete search history.

(56) References Cited

U.S. PATENT DOCUMENTS

| | | | |
|---|---|---|---|
| 4,950,432 A * | 8/1990 | Mehta et al. ............... 264/4.6 |
| 5,977,163 A | 11/1999 | Li et al. |
| 6,194,181 B1 | 2/2001 | Hofmann et al. |
| 6,204,388 B1 | 3/2001 | Danishefsky et al. |
| 6,211,412 B1 | 4/2001 | Georg et al. |
| 6,262,094 B1 | 7/2001 | Hoefle et al. |
| 6,365,749 B1 | 4/2002 | Kim et al. |
| 6,380,395 B1 * | 4/2002 | Vite et al. ............... 548/146 |
| 6,387,927 B1 | 5/2002 | Altmann et al. |
| 6,399,638 B1 | 6/2002 | Vite et al. |
| 6,441,025 B1 | 8/2002 | Li et al. |
| 6,441,186 B1 | 8/2002 | Nicolaou et al. |
| 6,518,421 B1 | 2/2003 | Li et al. |
| 6,576,651 B1 * | 6/2003 | Bandyopahyay et al. ... 514/365 |
| 6,650,599 B1 | 11/2003 | Takagi et al. |
| 6,670,384 B1 | 12/2003 | Bandyopadhyay et al. |
| 6,686,380 B1 | 2/2004 | Lee |
| 6,689,802 B1 * | 2/2004 | DiMarco et al. ............ 514/365 |
| 6,780,620 B1 | 8/2004 | Li et al. |
| 2002/0045609 A1 | 4/2002 | Ashley et al. |
| 2002/0169190 A1* | 11/2002 | Bandyopadhyay et al. . 514/365 |

FOREIGN PATENT DOCUMENTS

| | | |
|---|---|---|
| DE | 4138042.8 | 5/1993 |
| DE | 19542986.9 | 5/1997 |
| DE | 19639456.2 | 5/1997 |
| DE | 19636343.8 | 3/1998 |
| DE | 19645361.5 | 4/1998 |
| DE | 19645362.3 | 4/1998 |
| DE | 19647580.5 | 5/1998 |
| DE | 19701758 | 7/1998 |
| DE | 19707505.3 | 9/1998 |
| DE | 19713970 | 10/1998 |
| DE | 19720312 | 11/1998 |
| DE | 19821954 | 11/1998 |
| DE | 19726627 | 12/1998 |
| EP | 879 605 | 11/1998 |
| WO | 93/10121 | 5/1993 |
| WO | 97/19086 | 5/1997 |
| WO | 98/08849 | 3/1998 |
| WO | 98/22461 | 5/1998 |
| WO | 98/24427 | 6/1998 |
| WO | 98/25929 | 6/1998 |
| WO | 98/38192 | 9/1998 |
| WO | 98/47891 | 10/1998 |
| WO | 99/01124 | 1/1999 |
| WO | 99/02514 | 1/1999 |
| WO | 99/03848 | 1/1999 |
| WO | 99/07692 | 2/1999 |

(Continued)

OTHER PUBLICATIONS

Balog, A., et al., "Total Synthesis of (-)-Epothilone A", *Angew. Chem. Int. Ed. Engl.*, vol. 35, No. 23/24, 2801-2803 (1996).

(Continued)

*Primary Examiner*—Gollamudi S. Kishore
*Assistant Examiner*—Lakshmi Channavajjala
(74) *Attorney, Agent, or Firm*—Anastasia P. Winslow; Rena Patel

(57) ABSTRACT

A process for formulating certain epothilone analogs for parenteral administration is disclosed wherein the analog is dissolved in a mixture of at least 50% by volume tertiary-butanol in water, the mixture is lyophilized, the resulting lyophilized product is packaged in one vial with a sufficient amount of solvent comprising anhydrous ethanol and a suitable nonionic surfactant in a second vial. All steps are carried out with protection from light. In use, the contents of the second or diluent vial are added to the lyophilized product and mixed to constitute the epothilone analog and the resulting solution is diluted with a suitable diluent to produce a solution for intravenous injection containing the epothilone analog in a concentration of from about 0.1 mg/mL to about 0.9 mg/mL. A preferred surfactant is polyethoxylated castor oil and a preferred diluent is Lactated Ringer's Injection.

36 Claims, No Drawings

FOREIGN PATENT DOCUMENTS

| | | |
|---|---|---|
| WO | 99/27890 | 6/1999 |
| WO | 99/39694 | 8/1999 |
| WO | 99/42602 | 8/1999 |
| WO | 99/43320 | 9/1999 |
| WO | 99/43653 | 9/1999 |
| WO | 99/54319 | 10/1999 |
| WO | 99/67252 | 12/1999 |
| WO | 00/00485 | 1/2000 |
| WO | 00/31247 | 6/2000 |
| WO | 00/37473 | 6/2000 |
| WO | 00/49021 | 8/2000 |
| WO | 00/66589 | 11/2000 |

OTHER PUBLICATIONS

Bertini, F., et al., "Alkenes from Epoxides by Reductive Elimination with Magnesium Bromide-Magnesium Amalgam", *Chem. Commun.*, 144 (1970).

Bollag, D.M., et al., "Epothilones, A New Class of Microtubule-stabilizing Agents with a Taxol-like Mechanism of Action", *Cancer Res.* 55, No. 11, 2325-2333 (1995).

Fujisawa, T., et al., "Deoxygenation of Epoxides to Olefins with $FeCl_3$—n-BuLi System", *Chem. Lett.*, 883-886 (1974).

Fujiwara, Y., et al., "Reductive Coupling of Carbonyl Compounds to Olefins by Tungsten Hexachloride-Lithium Aluminum Hydride and Some Tungsten and Molybdenum Carbonyls", *J. Org. Chem.*, vol. 43, No. 12, 2477-2479 (1978).

Gladysz, J. A., et al., "Deoxygenation of Epoxides by Metal Atom Cocondensation", *J. Org. Chem.*, vol. 41, No. 22, 3647-3648 (1976).

Hofle, G., et al., "Epothilone A and B—Novel 16-Membered Macrolides with Cytotoxic Activity: Isolation, Crystal Structure, and Conformation in Solution", *Angew. Chem. Int. Ed. Engl.*, vol. 35, No. 13/14, 1567-1569 (1996).

Hofle, G., et al., "N-Oxidation of Epothilone A-C and O-Acyl Rearrangement to C-19 and C-21—Substituted Epothilones", *Angew. Chem. Int. Ed.*, vol. 38, No. 13/14, 1971-1974 (1999).

Inokuchi, T., et al., "Opening of Epoxides to Olefins or Halohydrins with Vanadium(II)-Tetrahydrofuran or Vanadium(III)-Tetrahydrofuran Complexes", *Synlett*, No. 6, 510-512 (1992).

Kowalski. R. J., et al., "Activities of the Microtubule-stabilizing Agents Epothilones A and B with Purified Tubulin and in Cells Resistant to Paclitaxel (Taxol®)" *J. Biol. Chem.*, vol 272, No. 4, 2534-2541 (1997).

Kupchan, S. M., et al., "Reductive Elimination of Epoxides to Olefins with Zinc-Copper Couple", *J. Org. Chem.*, vol. 36, No. 9, 1187-1190 (1971).

Martin, M. G., et al., "Epoxides as Alkene Protecting Groups. A Mild and Efficient Deoxygenation", *Tetrahedron Letters*, vol. 25, No. 3, 251-254 (1984).

McMurry, J. E., et al., "Reduction of Epoxides to Olefins with Low Valent Titanium", *J. Org. Chem.*, vol. 40, No. 17, 2555-2556 (1975).

McMurry, J. E., et al., "Some Deoxygenation Reactions with Low-Valent Titanium ($TiCl_3/LiAlH_4$)", *J. Org. Chem.*, vol. 43, No. 17, 3249-3254 (1978).

Meng, D., et al., "Remote Effects in Macrolide Formation Through Ring-Forming Olefin Metathesis: An Application to the Synthesis of Fully Active Epothilone Congeners", *J. Am. Chem. Soc.*, vol. 119, No. 11, 2733-2734 (1997).

Nicolaou, K. C., et al., "An Approach to Epothilones Based on Olefin Metathesis", *Angew. Chem. Int. Ed. Engl.*, vol. 35, No. 20, 2399-2401 (1996).

Nicolaou, K. C., et al., "Total Synthesis of Epothilone A: The Macrolactonization Approach", *Angew. Chem. Int. Ed. Engl.*, vol. 36, No. 5, 525-527 (1997).

Nicolaou, K. C., et al., "Designed Epothilones: Combinatorial Synthesis, Tubulin Assembly Properties, and Cytotoxic Action against Taxol-Resistant Tumor Cells", *Angew. Chem. Int. Ed. Engl.*, vol. 36, No. 19, 2097-2103 (1997).

Nicolaou, K.C., et al., "The Olefin Metathesis Approach to Epothilone A and Its Analogues", *J. Am. Chem. Soc.*, vol. 119, No. 34, 7960-7973 (1997).

Nicolaou, K. C., et al., "Total Syntheses of Epothilones A and B via a Macrolactonization-Based Strategy", *J. Am. Chem. Soc.*, vol. 119, No. 34, 7974-7991 (1997).

Nicolaou, K. C., et al., "Synthesis of Epothilones A and B in Solid and Solution Phase", *Nature*, vol. 387, 268-272 (1997).

Nicolaou, K. C., et al., "Synthesis of Epothilones A and B in Solid and Solution Phase" (Correction to Nature 387, 268-272 (1997)), *Nature*, 390, 100 (1997).

Raucher, S., et al., "Total Synthesis of (+)-Dihydrocostunolide via Tandem Cope-Claisen Rearrangement", *J. Org. Chem.*, vol. 51, No. 26, 5503-5505 (1986).

Sato, M, et al., "Reduction of Organic Compounds with Low-Valent Niobium ($NbCl_5/NaAlH_4$)", *Chem. Letters*, 157-160 (1982).

Schinzer, D., et al., "Total Synthesis of (-)-Epothilone A", *Angew. Chem. Int. Ed. Engl.*, vol. 36, No. 5, 523-524 (1997).

Schobert, R., et al., "Reduction and Isomerization of Oxiranes and α-Diazoketones by Various Early Transition Metallocenes", *Synlett*, vol. 8, 465-466 (1990).

Sharpless, K. B., et al., "Lower Valent Tungsten Halides. A New Class of Reagents for Deoxygenation of Organic Molecules", *J. Amer. Chem. Soc.*, vol. 94, No. 18, 6538-6540 (1972).

Su, D.-S., et al., "Total Synthesis of (-)-Epothilone B: An Extension of the Suzuki Coupling Method and Insights into Structure-Activity Relationships of the Epothilones", *Angew. Chem. Int. Ed. Engl.*, vol. 36, No. 7, 757-759 (1997).

Su, D.-S., et al., "Structure-Activity Relationships of the Epothilones and the First In Vivo Comparison with Paclitaxel", *Angew. Chem. Int. Ed. Engl.*, vol. 36, No. 19, 2093-2096 (1997).

Victory, S. F., et al., "Relative Stereochemistry and Solution Conformation of the Novel Paclitaxel-Like Antimitotic Agent Epothilone A", *Bioorg. Med. Chem. Letts.*, vol. 6., No. 7, 893-898 (1996).

Winkler, J. D., et al., "A Model For the Taxol (Paclitaxel)/ Epothilone Pharmacophore", *Bioorg. Med. Chem. Letts.*, vol. 6, No. 24, 2963-2966 (1996).

Yang, Z., et al., "Total Synthesis of Epothilone A: The Olefin Metathesis Approach", *Angew. Chem. Int. Ed. Engl.*, vol. 36, No. 1/2, 166-168 (1997).

Bollag, D., et al., "Epothilone, A New Structural Class Microtuble Stabilizer", Abstract, *Proc. Am. Assoc. Cancer Res.*, vol. 36, 86 Meet. 454 (1995).

Bollag, D., "Epothilones: Novel Microtuble-Stabilising Agents", *Expert Opin. Invest. Drugs*, vol. 6, No. 7, 867-873 (1997).

Bertinato, P., et al., "Studies Toward a Synthesis of Epothilone A: Stereocontrolled Assembly of the Acyl Region and Models for Macrocyclization", J. Org. Chem., vol. 61, No. 23, 8000-8001 (1996).

*Chemical & Engineering News*, "Epothilone Epiphany: Total Syntheses", vol. 74, No. 52, 24-26 (1996).
*Chemical & Engineering News*, "First Total Synthesis of Epothilone B", vol. 75, No. 13, 23 (1997).
*Chemical & Engineering News*, "Solid-Phase Epothilone Synthesis Used to Create Analog Library", vol. 75, No. 20, 33 (1997).
Claus, E., et al., "Synthesis of the C1-C9 Segment of Epothilons", *Tetrahedron Lett.*, vol. 38, No. 8, 1359-1362 (1997).
De Brabander, J., et al., "Towards a Synthesis of Epothilone A: Rapid Assembly of the C1-C6 and C7-C12 Fragments", *Synlett*, vol. 7, 824-826 (1997).
Gabriel, T. and Wessjohann, L., "The Chromium-Reformatsky Reaction: Asymmetric Synthesis of the Aldol Fragment of the Cytotoxic Epothilons from 3-(2-Bromoacyl)-2-Oxazolidinones", *Tetrahedron Lett.*, vol. 38, No. 8, 1363-1366 (1997).
Gerth, K., et al., "Epothilons A and B: Antifungal and Cytotoxic Compounds from *Sorangiusm cellulosum* (Myxobacteria) Production Physico-chemical and Biological Properties", *J. Antibiotics*, vol. 46, No. 6, 560-563 (1996).
Marshall, A., "Total Synthesis of Epothilone", *Nature Biotechnology*, vol. 15, No. 3, 205 (1997).
Meng, D., et al., "Studies Toward a Synthesis of Epothilone A: Use of Hydropyran Templates for the Management of Acyclic Stereochemical Relationships", *J. Org. Chem.*, vol. 61, No. 23, 7998-7999 (1996).
Meng, D., et al., "Total Syntheses of Epothilones A and B", *J. Am. Chem. Soc.*, vol. 119, No. 42, 10073-10092 (1997).
Mensching, S. and Kalesse, M., "Generation of Thiazoles by Column Dehydrogenation of Thiazolidines with $MnO_2$", *J. Prakt. Chem.*, vol. 339, No. 1, 96-97 (1997).
Mulzer, J. and Mantoulidis, A., "Synthesis of the C(1)-C(9) Segment of the Cytotoxic Macrolides Epothilon A and B", *Tetrahedron Lett.*, vol. 37, No. 51, 9179-9182 (1996).

Nicolaou, K., et al., "Chemistry, Biology and Medicine of Selected Tubulin Polymerizing Agents", *Pure Appl. Chem.*, vol. 71, No. 6, 989-997 (1999).
Nicolaou, K., et al., "Total Synthesis of Epothilone E and Related Side-chain Modified Analogues Via a Stille Coupling Based Strategy", *Bioorg. Med. Chem.*, vol. 7, No. 5; 665-697 (1999).
Schinzer, D., et al., "Studies Towards the Total Synthesis of Epothilones: Asymmetric Synthesis of the Key Fragments", *Chem. Eur. J.*, vol. 2, No. 22, 1477-1482 (1996).
Taylor, R. and Haley, J., "Towards the Synthesis of Epothilone A: Enantioselective Preparation of the Thiazole Sidechain and Macrocyclic Ring Closure", *Tetrahedron Lett.*, vol. 38, No. 12, 2061-2064 (1997).
Schinzer, D., et al., "Syntheses of (-)-Epothilone A", *Chem. Eur. J.*, vol. 5, No. 9, 2483-2491 (1999).
Schinzer, D., et al., "Syntheses of (-)-Epothilone B", *Chem. Eur. J.*, vol. 5, No. 9, 2492-2500 (1999).
Nicolaou, K. C., et al., "Synthesis and Biological Properties of C12, 13-Cyclopropylepothilone A and Related Epothilones", *Chemistry & Biology*, vol. 5, No. 7, 365-372 (1998).
Altmann, K.H., et al., "Epothilones and Related Structures—A New Class of Microtubule Inhibitors With Patent In Vivo Antitumor Activity," Biochim. Biophys Acta, 1470 (2000).
Nicolaou et al., "Total Synthesis of Epothilone E and Analogs with Modified Side Chains Through The Stille Coupling Reaction", Angew. Chem. Int. Ed. 37, 84-87 (1998).
Nicolaou et al., "Total Synthesis of Oxazole- and Cyclopropane-Containing Epothilone B Analogues by the Macrolactonization Approach", Chemistry, European Journal, vol. 3, No. 12, 1971-1986 (1997).
Nicolaou et al., "Chemical Biology of Epothilones", Angew. Chem. Int. Ed., 37, 2014-2045 (1988).

* cited by examiner

PARENTERAL FORMULATION FOR EPOTHILONE ANALOGS

CROSS-REFERENCE TO RELATED APPLICATION

This application claims priority from provisional application Ser. No. 60/264,228, filed Jan. 25, 2001, incorporated herein by reference in its entirety.

FIELD OF THE INVENTION

The present invention relates to an improved formulation for parenteral administration of certain epothilone analogs that are characterized by enhanced clinical efficacy.

BACKGROUND OF THE INVENTION

Epothilones are macrolide compounds having utility in the pharmaceutical field. For example, Epothilones A and B having the structures:

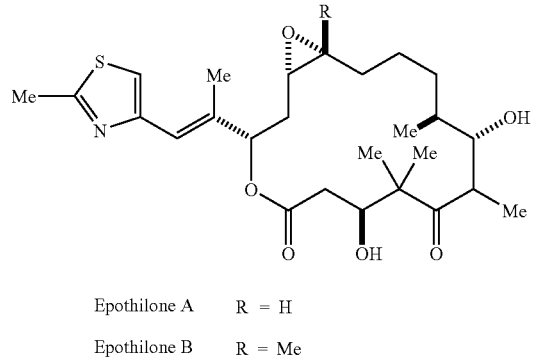

Epothilone A    R = H
Epothilone B    R = Me may be found to exert microtubule-stabilizing effects similar to paclitaxel (TAXOL®) and hence cytotoxic activity against rapidly proliferating cells, such as, tumor cells or other hyperproliferative cellular disease, see Hofle et al., *Angew. Chem. Int. Ed. Engl.*, Vol. 35, No. 13/14, 1567–1569 (1996); WO 93/10121 published May 27, 1993; and WO 97/19086 published May 29, 1997.

Derivatives and analogs of Epothilones A and B have been synthesized and may be used to treat a variety of cancers and other abnormal proliferative diseases. Such analogs are disclosed in Hofle et al., Id.; Nicolaou et al., *Angew Chem. Int. Ed. Engl.*, Vol. 36, No. 19, 2097–2103 (1997); and Su et al., *Angew Chem. Int. Ed. Engl.*, Vol. 36, No. 19, 2093–2097 (1997).

Analogs of the epothilones that have been found to have advantageous activity are represented by formula I:

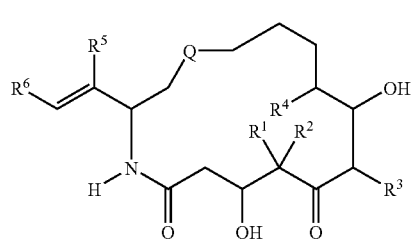

wherein the various symbols are as defined below. While these compounds possess significant therapeutic properties, they also present difficulties to those skilled in the art of pharmaceutical compounding, as a result of certain properties, as will be detailed hereinbelow. In accordance with the present invention, a formulation has been found whereby the epothilone analogs described above can be safely dispensed and administered via injection, without appreciable loss of potency.

SUMMARY OF THE INVENTION

The present invention describes a formulation and the preparation thereof for epothilone analogs represented by formula I.

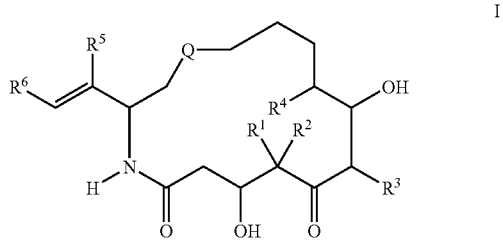

wherein the various symbols are as defined below. In the formulations of the present invention, the epothilone analog is initially solubilized with a mixture of tertiary-butanol and water and then lyophilized under optimized conditions. The lyophilized drug is reconstituted first with a mixture of a polyethoxylated castor oil surfactant and anhydrous ethanol, and thereafter diluted with Lactated Ringer's Injection to a concentration appropriate for administration.

DETAILED DESCRIPTION OF THE INVENTION

The process of the present invention provides an advantageous formulation for the administration of epothilone analogs represented by formula I:

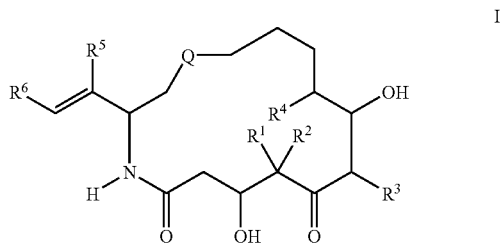

As used in formula I and throughout the specification, Q is selected from the group consisting of:

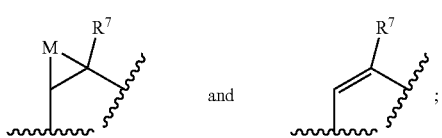

M is selected from the group consisting of oxygen, sulfur, $NR^8$, and $CR^9R^{10}$;

each $R^1$, $R^2$, $R^3$, $R^4$, $R^5$, $R^7$, $R^{11}$, $R^{12}$, $R^{13}$, $R^{14}$ and $R^{15}$ is, in independently, selected from the group consisting of hydrogen, alkyl, substituted alkyl, aryl, substituted aryl and heterocyclo, and wherein $R^1$ and $R^2$ are alkyl, they can be joined to form cycloalkyl;

$R^6$ is selected from the group consisting of hydrogen, alkyl, substituted alkyl, aryl, substituted aryl, cycloalkyl, heterocyclo and substituted heterocyclo;

$R^8$ is selected from the group consisting of hydrogen, alkyl, substituted alkyl, $R^{11}C{=}O$, $R^{12}OC{=}O$ and $R^{13}SO_2$; and each $R^9$ and $R^{10}$ is, independently, selected from the group consisting of hydrogen, halogen, alkyl, substituted alkyl, aryl, heterocyclo, hydroxy, $R^{14}C{=}O$, and $R^{15}C{=}O$.

The following are definitions of various terms used herein to describe the present invention. These definitions apply to the terms as they are used throughout this specification, unless otherwise limited in specific instances, either individually or as part of a larger group.

The term "alkyl" refers to optionally substituted straight- or branched-chain saturated hydrocarbon groups having from 1 to about 20 carbon atoms, preferably from 1 to about 7 carbon atoms. The expression "lower alkyl" refers to optionally substituted alkyl groups having from 1 to about 4 carbon atoms.

The term "substituted alkyl" refers to an alkyl group substituted by, for example, one to four substituents, such as, halo, trifluoromethyl, trifluoromethoxy, hydroxy, alkoxy, cycloalkyoxy, heterocylooxy, oxo, alkanoyl, aryl, aryloxy, aralkyl, alkanoyloxy, amino, alkylamino, arylamino, aralkylamino, cycloalkylamino, heterocycloamino, disubstituted amino in which the two substituents on the amino group are selected from alkyl, aryl, aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g., $SO_2NH_2$), substituted sulfonamido, nitro, cyano, carboxy, carbamyl (e.g., $CONH_2$), substituted carbamyl (e.g., CONH alkyl, CONH aryl, CONH aralkyl or instances where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Wherein, as noted above, the substituents themselves are further substituted, such further substituents are selected from the group consisting of halogen, alkyl, alkoxy, aryl and aralkyl. The definitions given herein for alkyl and substituted alkyl apply as well to the alkyl portion of alkoxy groups.

The term "halogen" or "halo" refers to fluorine, chlorine, bromine and iodine.

The term "ring system" refers to an optionally substituted ring system containing one to three rings and at least one carbon to carbon double bond in at least one ring. Exemplary ring systems include, but are not limited to, an aryl or a partially or fully unsaturated heterocyclic ring system, which may be optionally substituted.

The term "aryl" refers to monocyclic or bicyclic aromatic hydrocarbon groups having from about 6 to about 12 carbon atoms in the ring portion, for example, phenyl, naphthyl, biphenyl and diphenyl groups, each of which may be substituted.

The term "aralkyl" refers to an aryl group bonded to a larger entity through an alkyl group, for example, a benzyl group.

The term "substituted aryl" refers to an aryl group substituted by, for example, one to four substituents such as alkyl; substituted alkyl, halo, trifluoromethyl, trifluoromethoxy, hydroxy, alkoxy, cycloalkyloxy, heterocyclooxy, alkanoyl, alkanoyloxy, amino, alkylamino, dialkylamino, aralkylamino, cycloalkylamino, heterocycloamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by one or more members selected from the group consisting of halo, hydroxy, alkyl, alkoxy, aryl, substituted alkyl, substituted aryl and aralkyl.

The term "cycloalkyl" refers to optionally substituted saturated cyclic hydrocarbon ring systems, preferably containing 1 to 3 rings and 3 to 7 carbons per ring, which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more of the groups described above as substituents for alkyl groups.

The terms "heterocycle", "heterocyclic" and "heterocyclo" refer to an optionally substituted, unsaturated, partially saturated, or fully saturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents for the terms "ring system," "heterocycle," "heterocyclic," and "heterocyclo" include one or more substituent groups as described above for substituted alkyl or substituted aryl, and smaller heterocyclos, such as, epoxides, aziridines and the like.

The term "alkanoyl" refers to —C(O)-alkyl.

The term "substituted alkanoyl" refers to —C(O)-substituted alkyl.

The term "heteroatoms" shall include oxygen, sulfur and nitrogen.

The compounds represented by formula I form salts with a variety of organic and inorganic acids. Such salts include those formed with hydrogen chloride, hydrogen bromide, methanesulfonic acid, hydroxyethanesulfonic acid, sulfuric acid, acetic acid, trifluoroacetic acid, maleic acid, benzenesulfonic acid, toluenesulfonic acid and various others as are recognized by those of ordinary skill in the art of pharmaceutical compounding. Such salts are formed by reacting a compound represented by formula I in an equivalent amount of the acid in a medium in which the salt precipitates or in an aqueous medium followed by evaporation.

In addition, zwitterions ("inner salts") can be formed and are included within the term salts as used herein.

A particularly preferred epothilone analog within those represented by formula I is [1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4-aza-7-oxabicyclo[14.1.0]heptadecane-5,9-dione represented by formula II

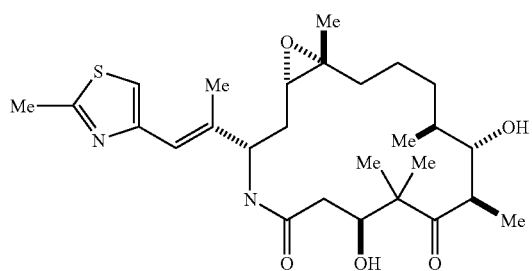

The compounds represented by formulae I and II above and their preparation are described in U.S. patent application Ser. No. 09/170,582, filed Oct. 13, 1998, the disclosure of which is incorporated herein by reference. The compounds represented by formulae I and II above may exist as multiple optical, geometric, and stereoisomers. While the compounds shown herein are depicted for one optical orientation, included within the present invention are all isomers and mixtures thereof.

The compounds represented by formulae I and II above are microtubule-stabilizing agents. They are thus useful in the treatment of a variety of cancers and other proliferative diseases including, but not limited to, the following:

carcinoma, including that of the bladder, breast, colon, kidney, liver, lung, ovary, pancreas, stomach, cervix, thyroid and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyoscarcoma;

other tumors, including melanoma, seminoma, teratocarcinoma, neuroblastoma and glioma;

tumors of the central and peripheral nervous system, including astrocytoma, neuroblastoma, glioma, and schwannomas;

tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma.

The compounds represented by formulae I and II above will also inhibit angiogenesis, thereby affecting the growth of tumors and providing treatment of tumors and tumor-related disorders. Such anti-angiogenesis properties of the compounds represented by formulae I and II will also be useful in the treatment of other conditions responsive to anti-angiogenesis agents including, but not limited to, certain forms of blindness related to retinal vascularization, arthritis, especially inflammatory arthritis, multiple sclerosis, restinosis and psoriasis.

Compounds represented by formulae I and II will induce or inhibit apoptosis, a physiological cell death process critical for normal development and homeostasis. Alterations of apoptotic pathways contribute to the pathogenesis of a variety of human diseases. Compounds represented by formulae I and II, as modulators of apoptosis, will be useful in the treatment of a variety of human diseases with aberrations in apoptosis including, but not limited to, cancer and precancerous lesions, immune response related diseases, viral infections, degenerative diseases of the musculoskeletal system and kidney disease.

Each of the compounds represented by formulae I and II may also be formulated or co-administered with other therapeutic agents that are selected for their particular usefulness in administering therapies associates with the aforementioned conditions. For example, each of the compounds of formulae I and II may be formulated with agents to prevent nausea, hypersensitivity, and gastric irritation, such as anti-emetics, and $H_1$ and $H_2$ antihistamines. The above therapeutic agents, when employed in combination with the compound of formulae I or II, may be used in those amounts indicated in the Physicians' Desk Reference (PDR) or as otherwise determined by one of ordinary skill in the art.

Furthermore, compounds of formulae I or II may be administered in combination with other anti-cancer and cytotoxic agents and treatments useful in the treatment of cancer or other proliferative diseases. Especially useful are anti-cancer and cytotoxic drug combinations wherein the second drug chosen acts in a different manner or different phase of the cell cycle, e.g., S phase, than the present compounds of formula I and II which exert their effects at the $G_2$-M phase. Example classes of anti-cancer and cytotoxic agents include, but are not limited to, alkylating agents, such as nitorgen mustards, alkyl sulfonates, nitrosoureas, ethylenimines, and triazenes; antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids, estrogens/antiestrogens, androgens/antiandrogens, progestins, and luteinizing hormone-releasing hormone antagonists, octreotide acetate;

microtubule-disruptor agents, such as ecteinascidins or their analogs and derivatives; microtubule-stabilizing agents such as paclitaxel (Taxol®), docetaxel (Taxotere®); plant-derived products, such as vinca alkaloids, epipodophyllotoxins, taxanes; and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators, and monoclonal antibodies. Compounds represented by formulae I and II may also be used in conjunction with radiation therapy.

Representative examples of these classes of anti-cancer and cytotoxic agents include, but are not limited to, mechlorethamine hydrochlordie, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred members of these classes include, but are not limited to, paclitaxel, cisplatin, carboplatin, doxorubicin, carminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, and leurosine.

Examples of anti-cancer and other cytotoxic agents include the following: cyclin dependent kinase inhibitors as found in WO 99/24416; and prenyl-protein transferase inhibitors as found in WO 97/30992 and WO 98/54966.

Without being bound by any theory regarding mechanism or morphology, the compounds represented by formulae I and II may also be used to treat conditions other than cancer or other proliferative diseases. Such conditions include, but are not limited to viral infections such as herpesvirus, poxvirus, Epstein-Barr virus, Sindbis virus and adenovirus; autoimmune diseases such as systemic lupus erythematosus, immune mediated glomerulonephritis, rheumatoid arthritis, psoriasis, inflammatory bowel diseases and autoimmune diabetes mellitus; neurodegenerative disorders such as Alzheimer's disease, AIDS-related dementia, Parkinson's disease, amyotrophic lateral sclerosis, retinitis pigmentosa, spinal muscular atrophy and cerebellar degeneration; AIDS; myelodysplastic syndromes; aplastic anemia; ischemic injury associated myocardial infarctions; stroke and reperfusion injury; restenosis; arrhythmia; atherosclerosis; toxin-induced or alcohol induced liver diseases; hematological diseases such as chronic anemia and aplastic anemia; degenerative diseases of the musculoskeletal system such as osteoporosis and arthritis; aspirin-sensitive rhinosinusitis; cystic fibrosis; multiple sclerosis; kidney diseases; and cancer pain.

The effective amount of a compound represented by formulae I and II may be determined by one of ordinary skill in the art, and includes exemplary dosage amounts for a human of from about 0.05 mg/kg/day to about 200 mg/kg/day, which may be administered in a single dose or in the form of individual divided doses, such as from 1 to about 4 times per day. Preferably, the compounds are administered in a dosage of less than about 100 mg/kg/day, in a single dose or in about 2 to about 4 divided doses. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The compounds represented by formulae I and II, particularly the latter, are disadvantageous from the viewpoint of compounding a suitable formulation for administration in that they possess very low solubility in aqueous media, rapidly degrade in contact with aqueous media, are sensitive to low pH when in solution, are light sensitive, are "Class D" cytotoxic and have exceptionally poor wetting characteristics. Any one or two of these characteristics might be compensated for in compounding a pharmaceutical formulation for intravenous administration, but the combination of all of them presents a formidable challenge to the pharmaceutical compounding chemist. Given the constraint that materials to be utilized in compounding an intravenous formulation must be approved for intravenous administration, the formulation provided in accordance with the present invention unexpectedly was found to be suitable for overcoming the disadvantageous properties of the subject epothilone analogs as noted above. Initially, because of the fact that the subject epothilone analogs are poorly soluble in aqueous media and, in fact, rapidly degrade in contact therewith, it was decided that they should be formulated in lyophilized form.

It has been found that a suitable media to form a solution of the subject compounds for lyophilization is a mixture of tertiary-butanol and water for injection. This mixture must be at least about 50% v/v, preferably from about 50% to about 80% v/v tertiary butanol to prevent degradation of the subject epothilone analogs. Further, due to the exceptionally poor wetting characteristics of the subject epothilone analogs, the initial solution must be effected utilizing a mixture of at least about 60% v/v, preferably from about 60% to about 95% v/v, tertiary butanol and water. Once the solution is made, the requisite amount of water or tertiary-butanol-water mixture can be added to achieve the final concentration for lyophilization as stated above.

It has unexpectedly been found that the stability of the subject epothilone analogs can be significantly enhanced by carrying out the preparation of the solution at a temperature below ambient, preferably from about 5° C. to about 15° C., more preferably about 5° C. Further, both the process of forming the solution and subsequent lyophilization are to be carried out in vessels such that the epothilone analogs are protected from exposure to light. It is also beneficial to carry out the lyophilization in comparatively small batches so that the epothilone analogs are exposed to an aqueous medium for a minimum amount of time.

The primary drying stage of lyophilization of the solution formed as described above is carried out at temperatures from about −10° C. to about −40° C., preferably about −25° C., under high vacuum, i.e., from about 50 millitorr to about 300 millitorr, preferably about 200 millitorr, for an extended period, i.e., from about 24 hours to about 96 hours, preferably about 48 hours. Lyophilization in this temperature range produces an amorphous product which is desirable for an intravenous preparation. Those of ordinary skill in the art will appreciate that conventional procedures, such as powder X-ray diffraction, can be utilized to confirm the amorphous nature of the lyophilized product.

The residual solvents in the product are removed by a secondary drying stage that is carried out at comparatively low temperatures, i.e., from about 10° C. to about 30° C., preferably about 25° C., under high vacuum, i.e., from about 50 millitorr to about 300 millitorr, preferably about 150 millitorr for an extended period, i.e., from about 24 hours to about 96 hours, preferably about 48 hours.

It has unexpectedly been found that the stability of lyophilized epothilone analogs described herein are not enhanced by excipients commonly utilized for such purposes, such as lactose, mannitol, dextran and the like. Certain of these excipients may actually have a negative effect on the stability of the lyophilized product (lyophile). Hence, the epothilone analogs formulated in accordance with the present invention are lyophilized neat, i.e., without any excipient.

The lyophilized epothilone analogs represented by formulae I and II are reconstituted with a mixture of equal parts by volume of Dehydrated Alcohol, USP and a nonionic surfactant, preferably a polyoxyethylated castor oil surfactant available from GAF Corporation, Mount Olive, N.J., under the trademark, Cremophor EL. The lyophilized product and vehicle for reconstitution are packaged separately in appropriately light-protected vials. To minimize the amount of surfactant in the reconstituted solution, only a sufficient amount of the vehicle is provided to form a solution having a concentration of about 2 mg/mL to about 4 mg/mL of the epothilone analog. Once dissolution of the drug is achieved, the resulting solution is further diluted prior to injection with a suitable parenteral diluent. Such diluents are well known to those of ordinary skill in the art. These diluents are generally available in clinical facilities. It is, however, within the scope of the present invention to package the subject epothilone analogs with a third vial containing sufficient parenteral diluent to prepare the final concentration for administration. A preferred diluent is Lactated Ringer's Injection. The final concentration for administration would preferably contain from about 0.1 mg/mL to about 0.9 mg/mL of the epothilone analog.

The final dilution of the reconstituted epothilone analog in the formulation of the invention may be carried out with other preparations having similar utility, for example, 5% Dextrose Injection, Lactated Ringer's and Dextrose Injection, Sterile Water for Injection, and the like. However, because of its narrow pH range, pH 6.0 to 7.5, Lactated Ringer's Injection is preferred. Per 100 mL, Lactated Ringer's Injection contains Sodium Chloride USP 0.6 g, Sodium Lactate 0.31 g, Potassium chloride USP 0.03 g and Calcium Chloride.2H$_2$O USP 0.02 g. The osmolarity is 275 mOsmol/L, which is very close to isotonicity.

The constituted preparation according to the present invention, i.e., the solution of the epothilone analog in the alcohol-surfactant vehicle, can be stored for up to about 24 hours before being further diluted for administration. It has been found that the incidence of allergic reactions encountered due to the presence of the surfactant in the formulation is minimized by keeping its concentration at the minimum necessary to effect solution of the epothilone analog. Further, the incidence of such reactions is about the same as has been experienced with other parenterally administered pharmaceuticals containing it, such as cyclosporine. This observed level of allergic reaction with the present formulation is significantly lower that has been experienced with certain other oncology agents, such as Paclitaxel. The final dilution is administered by intravenous infusion, typically over a period of up to an hour.

The following non-limiting example serves to illustrate the practice of the present invention.

EXAMPLE

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione, 9.86 g, was wetted/partially dissolved with 600 mL of a 9:1 mixture of tertiary butanol and Water for Injection USP which had been pre-cooled to 5° C. Once the drug powder had become completely wetted, dissolution was completed by the addition of 600 mL of a 1:9 mixture of tertiary butanol and Water for Injection and 766 mL of a 1:1 mixture of tertiary butanol and Water for Injection which likewise had been pre-cooled to 5° C. thereby making the final solution a 1:1 mixture. The dissolution was carried out under protection from light.

The solution formed above was promptly lyophilized in a Virtis INOTOP lyophilizer at −16° C. under light protectant conditions over a period of 48 hours. The resultant lyophilized product (lyophile) was then further dried at 15° C. under high vacuum for 48 hours. No detectable degradation of the drug was observed during these procedures. The lyophile was packaged under sterile conditions into 30 mL vials, each containing 10 mg of drug and standard excess to allow for vial/needle/syringe loss.

The lyophile is reconstituted with 5.5 mL of a 1:1 volume mixture of Dehydrated Alcohol USP and Cremophor EL®, which typically will be supplied with the drug in a separate vial, to achieve a final drug concentration of 2 mg/mL. Once dissolution is effected by gently swirling the vial, the resultant solution is diluted to achieve a concentration of 0.2 mg/mL by the addition of 9 mL of Lactated Ringer's for Injection for each milliliter of constituted drug product.

What is claimed is:

1. A process for formulating an epothilone analog represented by formula I:

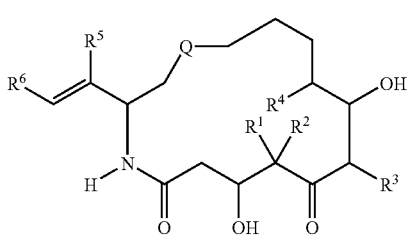

and/or a pharmaceutically-acceptable salt, geometric, optical, or stereoisomer thereof, wherein:

Q is

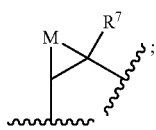

M is oxygen;

each $R^1$, $R^{2,}$ $R^{3,}$ $R^{4,}$ $R^{5,}$ and $R^7$ is, independently, selected from the group consisting of hydrogen, alkyl, substituted alkyl, aryl, substituted aryl and heterocyclo, and wherein $R^1$ and $R^2$ are alkyl, they can be joined to form cycloalkyl;

$R^6$ is selected from the group consisting of hydrogen, alkyl, substituted alkyl, aryl, substituted aryl, cycloalkyl, and heterocyclo;

and any salts, solvates, or hydrates thereof, comprising the following steps:

a) dissolving said epothilone analog in a mixture of at least about 50% by volume tertiary-butanol in water to form a solution;

b) performing primary drying of said solution at a temperature of from about −10° C. to about −40° C. under vacuum of from about 50 millitorr to about 300 millitorr for from about 24 hours to about 96 hours to form a primary lyophilized product; and c) performing secondary drying of the primary lyophilized product at a temperature of from about 10° C. to about 30° C. under vacuum of from about 50 millitorr to about 300 millitorr for from about 24 hours to about 96 hours to provide a lyophilized product of the epothilone analog.

2. The process of claim 1 wherein said epothilone analog is represented by formula II:

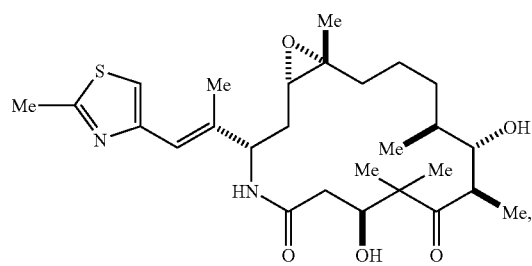

II and/or a pharmaceutically-acceptable salt, geometric, optical, or stereoisomer thereof.

3. The process of claim 1 wherein step a) comprises first, wetting said epothilone analog with a mixture of at least about 60% tertiary-butanol in water, and then adding sufficient water, or a mixture of tertiary-butanol and water, so that the resulting solution contains from about 2 mg/mL to about 30 mg/mL of said epothilone analog in a mixture of from about 50% to about 80% by volume tertiary-butanol in water.

4. The process of claim 2 wherein step a) comprises first, wetting said epothilone analog with a mixture of at least about 60% tertiary-butanol in water, and then adding sufficient water, or a mixture of tertiary-butanol and water, so that the resulting solution contains from about 2 mg/mL to about 30 mg/mL of said epothilone analog in a mixture of from about 50% to about 80% by volume tertiary-butanol in water.

5. The process of claim 3 wherein in step a) said epothilone analog is initially wetted with a mixture of from about 60% to about 95% by volume tertiary-butanol in water.

6. The process of claim 4 wherein in step a) said epothilone analog is initially wetted with a mixture of from about 60% to about 95% by volume tertiary-butanol in water.

7. The process of claim 2 wherein said primary drying in step b) is carried out at a temperature of from about −25° C. to −40° C. and a pressure of from about 200 to 300 millitorr.

8. The process of claim 2 wherein said secondary drying in step c) is carried out at a temperature of from about 25° C. to 30° C. and a pressure of from about 150 to 300 millitorr.

9. The process of claim 1, further comprising the step of:

d) packaging said lyophilized product of the epothilone analog in a first vial and packaging in a second vial a sufficient quantity of a mixture comprising at least one suitable nonionic surfactant and at least one dehydrated alcohol to effect reconstitution of the lyophilized product.

10. The process of claim 9 wherein the mixture comprises about equal parts by volume of anhydrous ethanol and the at least one nonionic surfactant.

11. The process of claim 9 wherein said epothilone analog is:

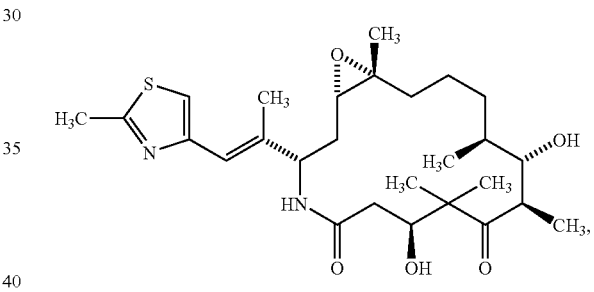

and/or a pharmaceutically-acceptable salt, geometric, optical, or stereoisomer thereof.

12. The process of claim 9 wherein said surfactant is polyethoxylated castor oil.

13. The process of claim 11 wherein said surfactant is polyethoxylated castor oil.

14. The process of claim 9 wherein said second vial contains an amount of said mixture sufficient to form a solution of from about 2 mg/mL to about 4 mg/mL of said epothilone analog therein.

15. A process for formulating an epothilone analog having the formula:

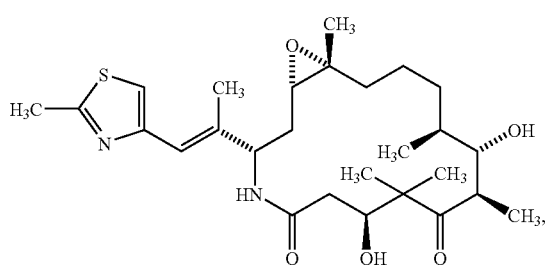

and/or a pharmaceutically-acceptable salt, geometric, optical, or stereoisomer thereof, comprising:
a) dissolving said epothilone analog in a mixture of tertiary butanol and water to form a solution, wherein the mixture comprises at least about 50% by volume tertiary butanol;
b) performing primary drying of said solution at a temperature, chamber pressure and period of time sufficient to form a primary lyophilized product; and
c) performing secondary drying of the primary lyophilized product at a temperature, chamber pressure and for a period of time sufficient to form a lyophilized product of the epothilone analog.

16. The process of claim 15, wherein said step a) of dissolving said epothilone analog is carried out at a temperature below ambient temperature.

17. The process of claim 15, wherein said step a) of dissolving said epothilone analog comprises first, wetting said epothilone analog with a mixture of at least about 60% by volume tertiary-butanol in water, and then adding sufficient water, or a mixture of tertiary-butanol and water, so that the resulting solution contains at least about 50% by volume tertiary-butanol in water.

18. The process of claim 15, wherein said step a) of dissolving said epothilone analog is carried out in the absence of an excipient.

19. The process of claim 15 wherein said primary drying in step b) is carried out at a temperature of from about $-10°$ C. to $-40°$ C. and at a chamber pressure of from about 50 to 300 millitorr for a period of up to about 96 hours.

20. The process of claim 19 wherein said secondary drying in step c) is carried out at a temperature of from about $10°$ C. to $300°$ C. and at a chamber pressure of from about 150 to 300 millitorr for a period of up to about 96 hours.

21. The process of claim 15, further comprising the step of:
d) packaging said lyophilized product of the epothilone analog in a first vial and packaging in a second vial a sufficient quantity of a solvent mixture to effect reconstitution of the epothilone analog, wherein the solvent mixture of the second vial comprises at least one suitable nonionic surfactant and at least one anhydrous alcohol.

22. A process for formulating an epothilone analog represented by formula II:

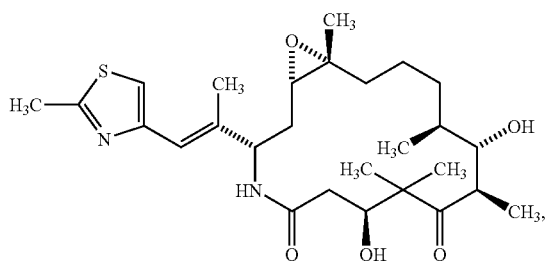

and/or a pharmaceutically-acceptable salt, geometric, optical, or stereoisomer thereof, comprising:
a) dissolving said epothilone analog to form a solution, comprising first, wetting said epothilone analog with a mixture of at least about 60% by volume tertiary-butanol in water, and then adding sufficient water, or a mixture of tertiary-butanol and water, so that the resulting solution contains at least about 50% by volume tertiary-butanol in water, wherein said step of dissolving is carried out at a temperature below ambient temperature;
b) performing primary drying of said solution at a temperature, chamber pressure and for a period of time sufficient to form a primary lyophilized product; and
c) performing secondary drying of the primary lyophilized product at temperature, chamber pressure and for a period of time sufficient to form a lyophilized product of the epothilone analog.

23. The process of claim 22 wherein,
step b) of primary drying of said solution is performed at a temperature of about $-10°$ C. to about $-40°$ C. under vacuum of from about 50 millitorr to about 300 millitorr for from about 24 hours to about 96 hours; and
step c) of secondary drying is performed at a temperature of from about $10°$ C. to about $30°$ under vacuum of from about 50 millitorr to about 300 millitorr for from about 24 hours to about 96 hours to provide a lyophilized product of the epothilone analog.

24. The process of claim 23 wherein,
step a) of dissolving said epothilone analog is carried out at a temperature of from about $-5°$ C. to about $15°$ C.

25. The process of claim 24 wherein,
step a) of dissolving said epothilone analog is carried out in the absence of an excipient.

26. The process of claim 24, further comprising the step of:
d) packaging said lyophilized product of the epothilone analog in a first vial and packaging in a second vial a sufficient quantity of a solution to effect reconstitution of the lyophilized epothilone analog, wherein the solution of the second vial comprises about equal amounts of at least one suitable nonionic surfactant and at least one anhydrous alcohol.

27. A pharmaceutical preparation comprising a lyophilized epothilone analog prepared according to claim 1.

28. A pharmaceutical preparation comprising a lyophilized epothilone analog prepared according to claim 2.

29. A pharmaceutical preparation comprising a lyophilized epothilone analog prepared according to claim 15.

30. A pharmaceutical preparation comprising a lyophilized epothilone analog prepared according to claim 20.

31. A pharmaceutical preparation comprising a lyophilized epothilone analog prepared according to claim 24.

32. A pharmaceutical product comprising at least a first and a second vial wherein the first vial contains a lyophilized epothilone analog prepared according to claim 2, and the second vial contains a sufficient quantity of a solution to effect reconstitution of the lyophilized epothilone analog, wherein the solution of the second vial comprises about equal amounts of at least one suitable nonionic surfactant and at least one anhydrous alcohol.

33. A method of treating a patient comprising, mixing the contents of the first and second vials of the pharmaceutical product of claim 32 to provide an epothilone analog solution, diluting the epothilone analog solution with a quantitiy of a suitable parenteral diluent to prepare an intravenous formulation, and administering the intravenous formulation to the patient.

34. A pharmaceutical product comprising at least a first and a second vial wherein the first vial contains a lyophilized epothilone analog prepared according to claim 15, and the second vial contains a sufficient quantity of a solution to effect reconstitution of the lyophilized epothilone analog, wherein the solution of the second vial comprises about equal amounts of at least one suitable nonionic surfactant and at least one anhydrous alcohol.

35. A method of treating a patient comprising, mixing the contents of the first and second vials of the pharmaceutical product of claim 34 to provide an epothilone solution, diluting the epothilone solution with a quantitiy of a suitable parenteral diluent to prepare an intravenous formulation, and administering the intravenous formulation to the patient.

36. The process of claim 15, wherein said step a) of dissolving said epothilone analog is carried out at a temperature in the range of from about 5° C. to about 15° C.

* * * * *